United States Patent
Knecht et al.

(10) Patent No.: US 9,733,264 B2
(45) Date of Patent: Aug. 15, 2017

(54) SUPPLY MODULE FOR AN AUTOMATED ANALYZER

(71) Applicant: Roche Molecular Systems, Inc., Pleasanton, CA (US)

(72) Inventors: Urs Knecht, Pfaeffikon (CH); Siegfried Mueller, Meierskappel (CH); Markus Rinderknecht, Adligenswil (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 81 days.

(21) Appl. No.: 14/565,001

(22) Filed: Dec. 9, 2014

(65) Prior Publication Data

US 2015/0093834 A1     Apr. 2, 2015

(51) Int. Cl.
*G01N 35/00* (2006.01)
*G01N 35/10* (2006.01)
*G01N 35/04* (2006.01)

(52) U.S. Cl.
CPC .......... *G01N 35/0099* (2013.01); *G01N 35/04* (2013.01); *G01N 35/1002* (2013.01); *G01N 35/00871* (2013.01); *G01N 2035/00346* (2013.01); *G01N 2035/00891* (2013.01); *G01N 2035/0465* (2013.01); *G01N 2035/0498* (2013.01); *Y10T 436/11* (2015.01)

(58) Field of Classification Search
CPC .............................. G01N 35/00; G01N 35/10
USPC .................................. 422/63–67; 436/43–54
See application file for complete search history.

(56) References Cited

U.S. PATENT DOCUMENTS

| | | | | |
|---|---|---|---|---|
| 4,554,839 A | * | 11/1985 | Hewett ................ | B01L 3/5085 422/561 |
| 4,766,082 A | * | 8/1988 | Marteau D'Autry .. | G01N 1/405 210/198.2 |
| 4,849,177 A | * | 7/1989 | Jordan .................... | B01L 3/508 206/521.7 |
| 4,925,629 A | * | 5/1990 | Schramm .............. | B01L 3/5085 422/417 |
| 4,965,049 A | * | 10/1990 | Lillig ................... | G01N 35/025 141/130 |
| 5,246,665 A | * | 9/1993 | Tyranski .............. | G01N 35/025 422/547 |
| 5,266,272 A | * | 11/1993 | Griner ................ | B01L 3/50853 211/126.1 |
| 5,279,797 A | * | 1/1994 | Burns .................... | B01L 3/505 206/221 |
| 5,282,149 A | * | 1/1994 | Grandone ........ | G01N 35/00732 422/67 |
| 5,482,839 A | * | 1/1996 | Ashihara ................ | G01N 33/53 356/244 |

(Continued)

FOREIGN PATENT DOCUMENTS

| | | |
|---|---|---|
| EP | 0517092 | 12/1992 |
| EP | 0632271 | 1/1995 |
| WO | 2009062722 | 5/2009 |

*Primary Examiner* — Arlen Soderquist
(74) *Attorney, Agent, or Firm* — Pamela C. Ancona

(57) ABSTRACT

A method is described for supplying consumables to an automated analyzer by providing at least one reagent and at least one solid consumable from a supply module which is docked to the analyzer, followed by undocking the supply module from the analyzer and removing it therefrom. Also described is a respective system and a supply module for supplying consumables to an automated analyzer.

15 Claims, 2 Drawing Sheets

(56) References Cited

U.S. PATENT DOCUMENTS

| | | | | |
|---|---|---|---|---|
| 5,519,635 A * | 5/1996 | Miyake | ............... | B01F 5/0475 |
| | | | | 422/504 |
| 5,585,068 A * | 12/1996 | Panetz | ............... | G01N 35/025 |
| | | | | 422/547 |
| 5,645,114 A * | 7/1997 | Bogen | ............... | B01L 3/0293 |
| | | | | 141/130 |
| 5,665,315 A * | 9/1997 | Robert | ............... | B01L 3/0293 |
| | | | | 204/401 |
| 5,746,976 A * | 5/1998 | Yamada | ............... | G01D 11/24 |
| | | | | 422/547 |
| 5,885,533 A * | 3/1999 | Savage | ............... | B01L 3/0293 |
| | | | | 137/614.03 |
| 5,928,952 A * | 7/1999 | Hutchins | ............... | B01J 19/004 |
| | | | | 422/561 |
| 5,948,360 A * | 9/1999 | Rao | ............... | G01N 30/24 |
| | | | | 422/63 |
| 5,993,741 A * | 11/1999 | Behnk | ............... | G01N 35/04 |
| | | | | 422/63 |
| 7,560,071 B2 * | 7/2009 | Nichols | ............... | B01L 3/565 |
| | | | | 414/222.01 |
| 8,734,720 B2 * | 5/2014 | Nichols | ............... | B01L 3/565 |
| | | | | 414/222.01 |
| 2007/0237675 A1 * | 10/2007 | Nichols | ............... | B01L 3/565 |
| | | | | 422/63 |
| 2009/0151479 A1 * | 6/2009 | Bartel | ............... | G06F 19/327 |
| | | | | 73/864.51 |
| 2009/0221059 A1 | 9/2009 | Williams et al. | | |
| 2009/0240370 A1 * | 9/2009 | Nichols | ............... | G01N 35/04 |
| | | | | 700/248 |
| 2009/0246081 A1 * | 10/2009 | Nichols | ............... | B01L 3/565 |
| | | | | 422/63 |

* cited by examiner

SUPPLY MODULE FOR AN AUTOMATED ANALYZER

CROSS-REFERENCES TO RELATED APPLICATIONS

The present application claims the benefit of priority under 35 U.S.C. §119 of EP 13197212.7, filed Dec. 13, 2013, the content of which is incorporated by reference herein in its entirety.

FIELD OF THE INVENTION

The present disclosure relates to the field of analytics, and in particular to methods, systems, and supply modules for loading solid and liquid consumables into systems for analyzing biological samples, such as automated analyzers.

BACKGROUND OF THE INVENTION

Analytical instruments in the field of in-vitro diagnostics, especially high-throughput analyzers, consume a high quantity of consumables within a relatively short period of time. Existing systems often require both consumable solid parts and liquids. The consumable solid parts include reaction vessels like plates or tubes in which samples are provided to the instrument and in which they are processed and analyzed. Liquid consumables include reagents for interacting with liquid samples and initiating biochemical reactions eventually leading to analysis of the samples. Liquid consumables may be provided within bulk containers or reagent cassettes. Solid as well as liquid consumables are usually separately loaded onto the system prior to use and removed therefrom in the same way after assay completion. Hence, analytical apparatuses commonly require loading of solid consumables and reagents within reagent containers in order to be able to perform the analytical process. These supplies are transported to and loaded onto the system, and, after usage, constitute waste that has to be removed from the system and discarded.

Especially in the case of high-throughput analyzers causing a high rate of test material consumption and, accordingly, a high production of waste, the above-described separate loading is typically labor-intensive and time-consuming. The process requires time slots during which processing or analysis of biological samples is idle and the user is occupied with the system. Moreover, user-system-interactions can be error-prone and necessitate specially trained personnel. Especially clinical samples, including the respective waste, often contain infectious biomaterial such as viruses or pathogenic bacteria. The samples, on the other hand, often need to be prevented from being cross-contaminated with other analytes in order not to cause false-positive results, particularly in the case of highly sensitive analysis methods such as Polymerase Chain Reaction (PCR) or immunochemical assays. In this context, manual waste handling steps may constitute an important safety issue since the risk of contamination for both system and user is increased. Furthermore, supply and waste collection units functionally coupled to the system with the aim of reducing manual handling steps usually take up extra space and require further automated transfer mechanisms.

Overall, processing speed as well as analytical flexibility are reduced significantly. This represents a major issue especially in the high-throughput sector, where the total system downtime due to resourcing plays an increasingly important role for operational as well as economical reasons.

Existing approaches include the usage of reagent packs. For instance, WO 2009/062722 discloses an analytical device which is supplied with liquids by a fluid pack, the latter carrying waste containers for fluid waste produced within the analyzer.

SUMMARY OF THE INVENTION

In one embodiment, a method is provided for supplying consumables to an automated analyzer having a housing. This method commences with providing a supply module including in a predefined geometrical arrangement at least one reagent and at least one set of solid consumables, and further including a mount for reversibly docking the supply module to the analyzer. The supply module is then reversibly docked to the analyzer using said mount and a receiving interface comprised by the housing of the analyzer. Further, at least one reagent and at least one solid consumable are supplied from the supply module to the analyzer prior to undocking the supply module from the analyzer and removing it therefrom. As detailed herein, the supply module having both a solid and a liquid consumable facilitates the workflow in an analytical system, reduces down-time and user intervention, and increases analytical throughput.

In another embodiment, a system is provided for supplying consumables to an automated analyzer. Said system includes a supply module having in a predefined geometrical arrangement at least one reagent and at least one set of solid consumables, and also a mount for reversibly docking the supply module to the automated analyzer. The system further includes an automated analyzer having a housing, the housing having a receiving interface for the supply module. Also included in the system is a work cell within the automated analyzer, the work cell being adapted to process a biological sample that may contain an analyte, and a robotic transferring device within the automated analyzer for retrieving the at least one reagent and/or the solid consumables from the supply module and transporting the at least one reagent and/or the solid consumables within the automated analyzer.

In another embodiment, a supply module is provided for supplying consumables to an automated analyzer, the supply module having at least one reagent and at least one set of solid consumables in a predefined geometrical arrangement, as well as a mount for reversibly docking the supply module to the automated analyzer.

BRIEF DESCRIPTION OF THE FIGURES

Other and further objects, features and advantages of the embodiments will appear more fully from the following description. The accompanying drawings, together with the general description given above and the detailed description given below, serve to explain the principles of the embodiments.

FIG. 1A shows an exploded view of the components of a supply module (1) and FIG. 1B shows a system for supplying consumables to an automated analyzer wherein the system includes a supply module (1) having, in a predefined geometrical arrangement, at least one reagent and at least one set of solid consumables, as well as a mount (4) for reversibly docking the supply module to the automated analyzer (24). The analyzer (24) includes a housing (25) comprising a receiving interface (26) for the supply module. The system also includes a work cell (27) within the analyzer, as well as a transfer module (28) having a robotic transferring device (29) for retrieving and transporting a reagent and/or consumable from the supply module within the automated analyzer. The mounts (4) may be engaged by corresponding recesses within the analyzer (30). The system also includes a fluidic connection (31) between the supply module and the analyzer, e.g., via the tubes (22) that extend from the ports to and through the mounts and through a port in the respective recesses of the analyzer. Also included is an electronic communication link (32) between the supply module and the analyzer. Moreover, the system also includes an electronic visual display (33) on the supply module and/or the automated analyzer.

DETAILED DESCRIPTION OF THE INVENTION

Figure 1A:
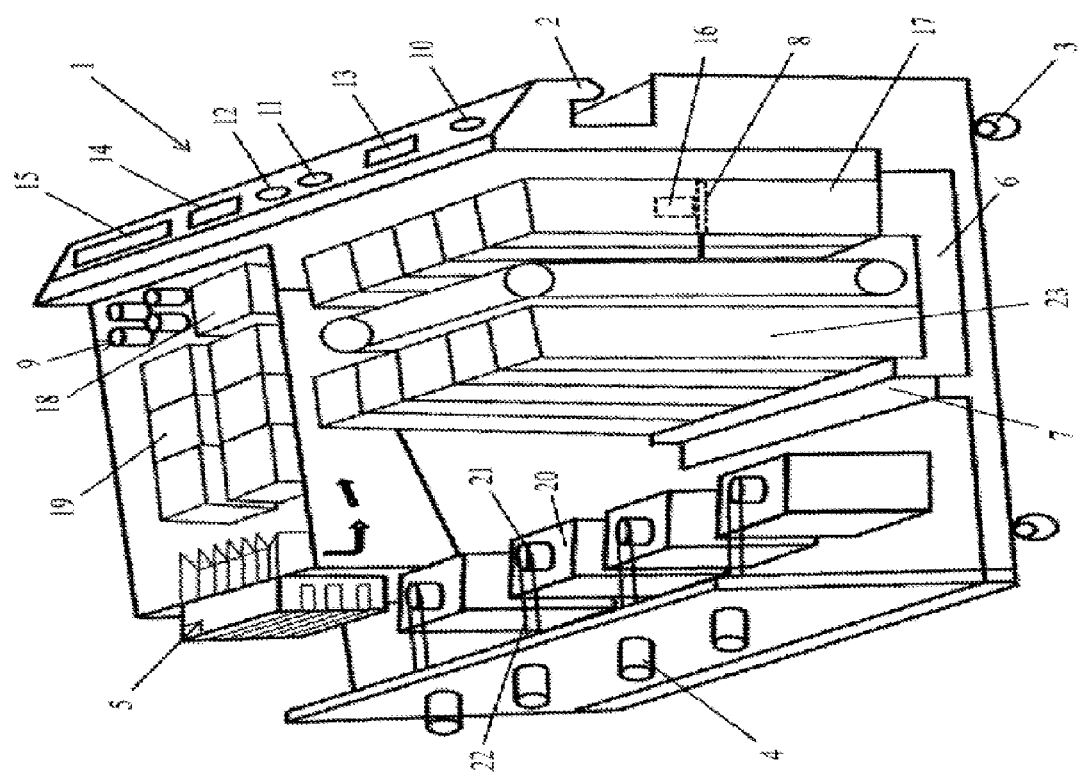
FIGS. 1A-B show an exploded view of the components which make up an example of a device and a system including the device.
Figure 1B:
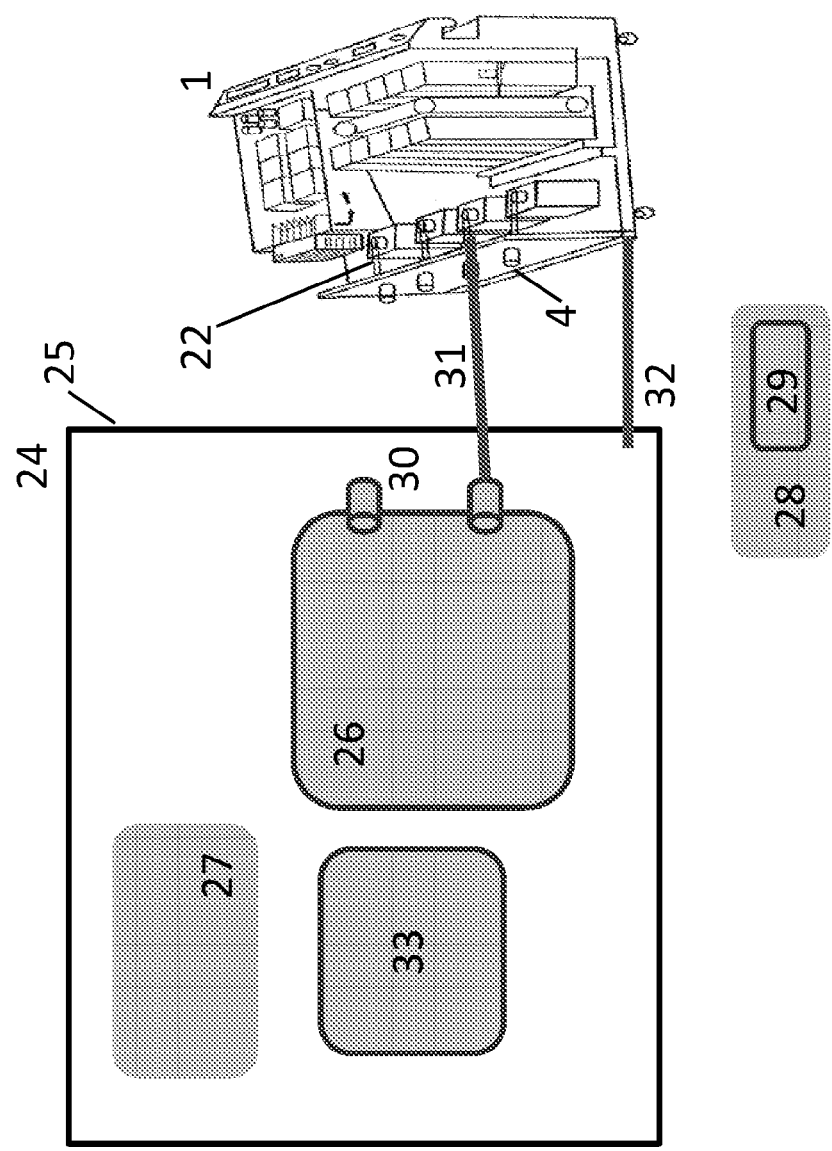

By way of illustration, specific exemplary embodiments in which the invention may be practiced now are described.

In one embodiment,

In a first aspect, a method is described for supplying consumables to an automated analyzer comprising a housing, the method comprising the steps of:

a) providing a supply module comprising in a predefined geometrical arrangement at least one reagent and at least one set of solid consumables, and further comprising a mount for reversibly docking the supply module to the analyzer b) reversibly docking the supply module to the analyzer using said mount and a receiving interface comprised by the housing of the analyzer c) supplying from the supply module to the analyzer at least one reagent and at least one solid consumable d) unlocking the supply module from the analyzer and removing it therefrom.

In contrast to other methods in the art, the method described herein enables the skilled person using an automated analyzer to reduce the time in which the system is idle due to resupply of reagents and solid consumables and in some embodiments the disposal of waste. In the method described herein, all required supplies are delivered to the analyzer via a single supply module, thus enabling one-step loading or exchange of liquids and solid consumables.

Furthermore, the required components can be loaded onto or prepared in the supply module offline, i.e. separately from the analyzer and hence not interfering with processing and/or analytic activities performed by the analyzer. This measure further reduces the time in which the analyzer is idle.

In addition to the simplified loading and unloading procedure, transport of the consumable system components is also facilitated, since they are all provided in one module. Embodiments in which the supply module has enhanced mobility, e.g. being portable or comprising wheels or the like, are particularly advantageous in this respect. Such supply modules allow for fast and convenient transport of the consumable system components, within a facility such as a clinic, or even between facilities by shipping.

The supply modules described herein can be adapted to the needs of a given automated analyzer. This accounts for the contents of the supply modules, but also for their specific setup. In other words, not only the specifically required consumable components such as reagents and solid components, and in some embodiments the respective waste containers, can be selected according to the automated analyzer in question, but for instance also the supply module's setup such as a specific docking system compatible with a counterpart comprised by the respective automated analyzer.

In comparison to analyzers in which reagents and solid consumables are spread throughout the system, the method described herein may also contribute to efficient usage of the available space in an automated analyzer, since only one interface is required. Thus, the other parts or compartments of the automated analyzer can be arranged without having to consider the respective space taken up by the different reagents and solid consumables. Additionally, the single interface has the advantage that the process of loading or unloading is facilitated as compared to systems with multiple sites for resupplying solid consumables and reagents and in some embodiments collecting waste.

The one-step loading or unloading described above further reduces the physical interaction between user and analyzer, thus minimizing the risk of contamination for both user and analyzer/sample. Consequently, supplying of solid consumables and reagents to the analyzer and in some embodiments the collection of waste does not demand an equally high level of training from the user as other methods in the art. Furthermore, since each physical interaction between user and automated analyzer is a potential error source, for example, bearing the risk of loading reagents or solid consumables onto the wrong module, the method described herein also reduces the risk of human errors by minimizing physical interaction.

As used herein, a "consumable" is understood to be a disposable system component which is introduced recurrently into an analytical system for use in an analytical test or the preparation of the respective biological samples. A consumable may in some embodiments be used a single time before being replaced, or it may in other embodiments be used multiple times. The term "consumables", as used herein, encompasses both liquid and solid consumables.

"Solid consumables" comprise components that need to be replaced after one or several uses. Examples of solid consumables include pipette tips, tip racks, vessels such as tubes or multiwell plates, containers such as waste containers for solid and/or liquid waste, cuvettes, caps or other closures for vessels or other containers, and the like. A "set of solid consumables" means a group of solid consumables of the same type, e.g. disposable pipette tips, or sample vials of a specific type, or processing vessels, or analysis vessels, and the like. In this respect, multiwell plates may be used whose dimensions follow international standards such as the SBS (Society for Biomolecular Sciences) or ANSI/SLAS (American National Standards Institute/Society for Laboratory Automation and Screening) standards.

The term "reagent" or "liquid consumable" are used interchangeably herein and indicate a composition required for treatment of a sample. Reagents may be any liquid, e.g. a solvent or a chemical solution, which needs to be mixed with a sample and in some cases with another reagent, for instance, for a reaction to occur which may enable detection of an analyte. A reagent may, for example, be a diluting liquid, including water. It may comprise an organic solvent, it may comprise a detergent, or it may comprise a buffer substance. Reagents may also be dry reagents adapted to be dissolved by a sample, another reagent or a diluting liquid. A reagent in the stricter sense of the term may be a liquid solution containing a reactant, typically a compound or agent capable of binding to or chemically transforming one or more analytes present in a sample. Examples of reactants are enzymes, enzyme substrates, conjugated dyes, protein-binding molecules, nucleic acid binding molecules, nucleic acid amplification reagents such as primers, probes or nucleoside triphosphates, antibodies, chelating agents, promoters, inhibitors, epitopes, antigens, and the like. Further, the term "reagents" may also comprise suspensions, such as suspensions of binding particles for biological materials or other particles. Reagents may further comprise emulsions. A reagent may in the method described herein be transferred from the supply module to the automated analyzer directly as a liquid, for example, by pumping it through a tube system, or it may be transferred contained inside a reagent container, the latter itself being a solid consumable that may be removed from the analyzer when no reagent is left therein.

The automated analyzer comprises a "housing" which at least partially encloses the system components of the automated analyzer. In some embodiments, the housing completely encloses the components of the analyzer. The housing separates the components from the outside of the analyzer and thus from potential sources of contamination, possibly leading to false analytical results. On the other hand, biological material such as clinical samples often contain infectious agents, such that the housing also reduces the risk of infection of the technical personnel with such material. The housing can be made of a variety of materials including, for example, metal and/or plastic. It can be transparent or non-transparent, or it can comprise transparent elements such as a window allowing a person to visually monitor certain processes within the automated analyzer from the outside. The analyzer may also comprise preanalytical components for preparation of a biological sample. Performing both preanalytical preparation and analysis of the prepared sample within the same housing minimizes exposure of potentially infectious sample material and/or material that is sensitive to contamination and facilitates the workflow.

The housing comprises a "receiving interface", which constitutes a gate that permits physical communication between the inside and the outside of the analyzer. In some embodiments, the receiving interface comprises a lid that can be manually or automatically opened and closed in order to transfer components or samples in- and outside of the automated analyzer. The receiving interface in some embodiments comprises docking elements for facilitating the docking of the supply module described herein. Such docking elements may e.g. comprise mounts, cables, liquid connections, tubes, pipes, sockets, hooks, magnets, and the like.

The "supply module" described herein is an exchangeable physical component for an automated analyzer, the module carrying liquid and solid consumables for supply or resupply of the automated analyzer. The supply module is a container in which the liquid and solid consumables are arranged in a predefined geometrical arrangement. The supply module is not limited to a specific shape or material. It can contain the consumables in one or more layers. Materials that the supply module may be made of comprise metal or plastics such as polypropylene (PP), or the like. The supply module can have different shapes and geometries. It may be a sliding module such as for instance a drawer, or a plug-in module like a cartridge. In other embodiments, it may be a trolley that may comprise multiple levels. Other variations and properties are possible, some of which are exemplified herein.

As used herein, a "predefined geometrical arrangement" is the structure in which the liquid consumables and the solid consumables are assembled within the supply module. This structure allows the analyzer to locate the position in which a consumable is held without requiring a sensor or the like. However, such a sensor may also be included in the analyzer. In some embodiments, the predefined geometrical arrangement comprises columns and rows of solid consumables and/or reagent containers which are in some embodiments arranged perpendicular to each other. Such arrangements are in some embodiments two-dimensional matrices of 3×4, 4×4, 3×6, 4×6, 6×6, 6×8, 8×8, or other possible matrices. The predefined geometrical arrangement may also extend into all three dimensions e.g. by stacking solid consumables and/or reagent containers or by comprising multiple levels like in embodiments in which the supply module is a trolley with multiple shelves. Furthermore, the predefined geometrical arrangement may relate to subgroups of the consumables held within the supply module. For instance, vessels such as reaction vials may be grouped in one structure such as a row, while racks containing pipette tips may be arranged in a different row elsewhere in the supply module. Again, such (sub)grouping may facilitate the controlled retrieval of the consumables by a robotic transferring device comprised by the automated analyzer, since the position of the different consumables is known and can e.g. be transmitted to a control unit and/or data management unit which is/are in some embodiments comprised by the automated analyzer and/or the supply module. Hence, as an example, multiple grouped consumables of the same type, such as a plurality of reaction vials, can be retrieved from the supply module into the analyzer in a quick and efficient manner. In embodiments where the supply module also collects waste from the analyzer, the waste container or containers within the supply module may be also separated from the unused consumables to be supplied to the analyzer, so as to further reduce the risk of cross-contamination.

The "robotic transferring device" comprises at least a robotic manipulator and/or a transfer system for solid consumables as described herein. This is sufficient, for example, in embodiments where no reagent is transferred from the supply module to the automated analyzer such as by pressure difference like pumping or suctioning through a fluidic connection like a tube system, but where reagent is transferred by introducing a reagent container filled with the respective reagent from the supply module into the automated analyzer. In other embodiments, the robotic transferring device further comprises a fluidic connection as described herein. The robotic transferring device may for instance comprise a robotic manipulator. In this context, a "robotic manipulator" is an automated manipulator configured to manipulate solid consumables including solid waste. In some embodiments, the robotic manipulator is a gripper that picks up a solid consumable at a certain point within the supply module and transfers it to the analyzer, or in the case of solid waste, retrieves it from the automated analyzer and transfers it to a solid waste container inside the supply module. In some embodiments, it can be moved laterally (along an x- and or y-axis) and vertically (along a z-axis). In some embodiments, the robotic manipulator can be moved within a part or all of the automated analyzer and/or the supply module. In order to be moveable, the robotic manipulator can e.g. be flexibly suspended and/or comprise a flexible robotic arm. For instance, the lateral movement can be facilitated by a rotatable robotic arm fixed e.g. to the bottom or the ceiling of the automated analyzer. Vertical movement can e.g. be achieved by a telescope arm. Also, the robotic manipulator can comprise a bipartite robotic arm rotatable at its base e.g. at the bottom of the automated analyzer, wherein the two parts of the arm are attached to each other via a hinge or another type of joint. By combined movement of the hinge and rotation of the arm at its base, the robotic manipulator may be moveable in all directions. In order to handle solid consumables such as vessels or vessel holders, it may comprise gripper arms. In such embodiments, the robotic manipulator is a gripper. Alternatively or additionally, the robotic manipulator can comprise means to apply a vacuum or at least negative pressure. Such a structure can for instance be or comprise a vacuum cup. In some embodiments, more than one robotic manipulator is used. For instance, two, three or four robotic manipulators may act simultaneously or at different times. Also in some embodiments, the analyzer comprises a dedicated robotic manipulator for each of the analyzer itself and the supply module. Alternatively or additionally, the supply module may itself comprise a robotic manipulator for transferring fresh solid consumables into the analyzer and/or to collect waste from the same. Robotic manipulators may also be used for transferring reagents contained inside a container, such as for resupplying a reagent to a work cell by transferring a respectively filled container from the supply module to the work cell by a robotic manipulator. The same accounts for the collection of solid waste in the form of emptied reagent containers from the automated analyzer to the supply module.

Other transfer mechanisms for solid consumables are possible. For instance, either the automated analyzer, or the supply module, or both may comprise a transfer system for solid consumables including reagent containers. Such a transfer system may comprise or essentially consist of a conveyor such as a band conveyor, a roller conveyor, a pneumatic conveyor, a vibrating conveyor, a vertical conveyor such as a lift, a spiral conveyor, or the like. The transfer system can also comprise or essentially consist of a surface with an integrated transport mechanism such as a hover cushion or a magnetic surface. In other embodiments, the transfer system can comprise or essentially consist of a rail system. Combinations of the above-mentioned transfer systems are possible. For instance, a robotic gripper comprised by the supply module places a solid consumable retrieved from the supply module on a conveyor band within the automated analyzer, and after transport on the latter to a work cell, the solid consumable is picked up and placed in the correct position within the work cell by a further robotic gripper comprised by the automated analyzer.

A "control unit" of an automated analyzer or a supply module may be a separate unit or may be an integral part of the respective device. The control unit controls the automated analyzer in a way that the necessary steps for the assay protocols are conducted. That means the control unit, for example, instructs the automated analyzer to conduct certain pipetting steps to mix the sample with reagents or the control unit controls the automated analyzer to incubate the sample mixtures for a certain time and the like. The control unit may receive information from a data management unit regarding which test has to be done with a certain sample and based thereon may determine the steps the automated analyzer has to perform. With regard to the management of consumables, the control unit may monitor the amount and consumption of liquid and solid consumables, for instance, by storing such data in a data management unit and retrieving it therefrom. The control unit may further monitor the status of liquid and solid consumables within the automated analyzer. This may involve sensor systems, such as liquid level detection (LLD) in reagent containers. LLD can be performed using different principles, for instance, based on capacitive, resistive, or (ultra)sonic measurements, or a combination of the foregoing. For solid consumables, electromechanical, optical or inductive sensor systems, or the like, may be used. For instance, a light barrier in a predefined space for a pipette tip rack may indicate to the control unit the presence or absence of a pipette tip rack. Likewise, this information may be obtained by a mechanical contact triggering an electric signal, for example, by closing an electric circuit, by changing electric properties like resistance, inductivity, or the like. Sensor systems for monitoring both liquid and solid consumables may include visual monitoring such as by a camera, wherein a software of the control unit analyzes the images and thereby recognizes the status of the consumables. For instance, the camera may analyze the image of a rack filled with pipette tips by counting the number of remaining pipette tips. Based on this information, the control unit may determine when the exchange of the corresponding rack is due, or in some embodiments also when it is estimated to become due. This may likewise be achieved by a logic employed by the control unit, wherein the control unit monitors how many pipette tips have already been removed since the corresponding rack was provided to the system bearing a complete set, i.e. a known number, of pipette tips. In the case of a supply module, the control unit may also comprise sensors as described for the control unit of the automated analyzer. For instance, in embodiments where liquid reagents are supplied from a container in the supply module to the analyzer using a liquid connection such as tubing or hoses, LLD in the supply module may monitor the fill status of the respective container and determine when a refill or exchange of that container becomes or is about to become due. Similarly, electromechanical or optical sensors may determine the presence or absence of specific solid consumables. Such embodiments bear the advantage that the control unit of the supply module is not dependent on information regarding the already transferred amount of consumables in order to determine how many of the respective consumables must still be present in the supply module. For instance, it may be possible that certain consumables are removed manually by laboratory personnel when the supply module is in an offline mode and thus possibly does not detect the removal. For those cases, it is advantageous if a sensor system detects and indicates to the control unit of the supply module what quantity of which type of consumables is present in the supply module. The control unit of the supply module may also determine the transfer of which consumables or in some embodiments waste needs to be initiated, in some embodiments also based on information from a data management unit. In embodiments where both the analyzer and the supply module have a control unit, the respective control units may electronically communicate with each other. This may be achieved by an electronic communication link between the supply module and the automated analyzer or their control units, respectively. Such an electronic communication link may include wiring or wireless data transfer such as by infrared, bluetooth, or the like. A wireless connection bears the advantage of potential communication even while the supply module may be physically separated from the analyzer, such as when being refilled manually or when being recharged at a battery recharging station. In embodiments involving a communication link, the control unit of the automated analyzer may analyze, as detailed above, which consumables need to be provided, removed or exchanged, and in some embodiments whether waste needs to be collected by the supply module. This information may trigger a request from the control unit of the automated analyzer to the control unit of the supply module, such that the latter may provide, retrieve or exchange the requested consumable or consumables. In turn, the supply module may transmit information to the automated analyzer regarding which consumables are available within the supply module and in what quantity. This allows for a highly coordinated supply and/or exchange of reagents and solid consumables, and for the timely exchange of the supply module itself before or when it runs out of unused consumables, or in some embodiments before or when the waste container or containers of the supply module is or are full. Besides such functions of recognition and inventory monitoring, the electronic communication may also allow for surveillance of the loading and unloading procedures, or for control and possibly regulation of the temperature within the supply module and/or the automated analyzer and/or the receiving interface comprised by the housing of the analyzer.

In certain embodiments, the control unit might be integral with the data management unit or may be embodied by a common hardware. The control unit may be embodied as a programmable logic controller running a computer-readable program, in some embodiments provided with instructions to perform operations in accordance with a process operation plan.

A "data management unit", in some embodiments by means of a "test request database" comprised by it, allows relating sample tube identification in the automated analyzer with the assay or assays to be conducted with the sample contained in the sample tube. The one or more analytical tests to be conducted with a particular sample are called a test request. In the case of a supply module, the data management unit may allow identification of the type and location of solid consumables and reagents contained in the supply module. This information may be dynamic, such that monitoring of the type, location and number of consumables within the supply module is possible, as described above. Likewise, the data management unit may contain and update data regarding waste taken up by the supply module from the automated analyzer. The data management unit is in many embodiments connected to a LIS (laboratory information system) and/or a HIS (hospital information system). The data management unit (DMU) can be a unit within or co-located with the automated analyzer or the supply module, e.g. it can be part of the control unit. Alternatively the DMU can be a unit remotely located from the analyzer or the supply module, e.g. can be embodied in a computer connected via a network to the automated analyzer. In some embodiments, an RFID chip may serve as a data management unit. RFID chips are capable of storing information readable and writable by RFID readers/writers that may be comprised by the analyzer. For instance, the control unit of the supply module may write, with an RFID writer, information about the consumable it contains on an RFID chip with which the supply module is tagged, and an RFID reader comprised by the analyzer may read and analyze this information such that the control unit of the analyzer may determine which of the consumables contained in the supply module are needed by the analyzer and initiates the respective transfer.

The supply module may further comprise a steering unit such as a computer which may autonomously, i.e. without permanent external steering, direct the supply module to the automated analyzer or other places. For instance, the supply module may need to be charged in embodiments involving an energy source such as a rechargeable battery as a power supply for electronic functions such as the control unit. Said control unit may recognize a low charging status of the battery and thus trigger the steering unit to direct the supply module to a charging station. Also in an embodiment, the steering unit may direct the supply module from the analyzer to a refill station in case it has to be refilled with consumables or in case its waste containers are full and need to be replaced. The supply module may replace or refill consumables, for example, by means of a robotic transferring device as described herein. The steering unit may, for convenience, also allow human intervention by programming predetermined routes that need to be routinely followed by the supply module, such as between the analyzer and an automated refill station or a site of manual refilling or exchanging. Such "intelligent" autonomous or semi-autonomous supply modules further reduce the need of human work force and increase the walk-away time for laboratory staff.

"Reversibly docking" means attaching objects to each other with the possibility of subsequent or later undocking. For instance, the supply module can be reversibly docked to the analyzer by any suitable "mount" such as latches, force fit (e.g. by friction/sticky surfaces), form fit (e.g. bolting, bayonet coupling, snap fitting, an undercut in the casting), hook-and-loop fastening, pressure (e.g. exerted manually or by a robotic arm, or applying a vacuum), magnetism, or other means. The supply module can be reversibly docked to the analyzer either directly or indirectly. "Reversibly docking" implies that the undocking can be easily carried out without destroying or damaging any of the involved objects.

In some embodiments of the method described herein, the supply module further comprises at least one waste container, and step c) further comprises collecting waste from the analyzer in at least one waste container of the supply module.

The term "waste container", as used herein, means a container arranged to receive waste collected from the analyzer. The waste container can be a container for liquid or solid waste, while the supply module described herein may contain only a liquid waste container; only a solid waste container, or both, or none of the above.

A "liquid waste container" is a container for collecting liquid that is no longer needed in an isolation or analytic process. Such a container can be made of different materials, comprising e.g. metal or plastics, and is not restricted to a specific shape. If, for example, the container is made of plastic, its production process in some embodiments includes injection molding, such that fastenings may be introduced during the production steps. The container is in some embodiments made of polypropylene. As known to the person skilled in the art, a suitable molding tool is used for production of the liquid waste container. The material used for producing a liquid waste container must be suitable to take up the respective liquid or liquids, e.g. it must be sufficiently resistant to acid in case the liquid waste produced by the analyzer is known or expected to have a considerably acidic pH. Such adaptions are within the knowledge of the person skilled in the art.

A "solid waste container" is a container for solid elements that are no longer needed in the analyzer. In many cases, this concerns solid consumables used one or more times in a process within the analyzer. As described previously, some solid consumables are used only once and are then discarded in order to avoid cross-contamination. Such solid waste is transferred from the analyzer by a suitable mechanism such as a robotic gripper to the supply module, where it is collected in a respective solid waste container. As in the case of the liquid waste container, it can be made of different materials, comprising e.g. metal or plastics. Its shape and size are restricted only in so far as it has to fit into the supply module and have dimensions that are sufficiently large to take up the required type or types of solid waste from the analyzer. For instance, if multiwell plates are to be discarded, the dimensions of the waste container allow the transfer of at least one multiwell plate into the solid waste container. In other words, the waste container has dimensions which are not smaller than the discarded solid consumables it is intended to take up. In this respect, multiwell plates may be used whose dimensions follow international standards such as the SBS (Society for Biomolecular Sciences) or ANSI/SLAS (American National Standards Institute/Society for Laboratory Automation and Screening) standards.

Such embodiments further increase the number of advantages conferred by the method described herein. In addition to the simplified workflow, transport etc. relating to loading fresh consumables into the analyzer, the workflow may be further streamlined by including the disposal of solid and/or liquid waste in the method. As described above, a reduced number of physical interventions between user and system contribute to the reduction of errors and contamination of both analyzer and technical personnel. This also accounts for the procedure of waste disposal. In embodiments where the same supply module is responsible for the supply of fresh consumables as well as the disposal of used consumables, the procedures may be performed in a coordinated manner. For instance, if a used multiwell plate is discarded from the analyzer into the solid waste container of the supply module, then a control and/or data management unit comprised by the analyzer and/or the supply module may initiate the supply of a fresh multiwell plate from the supply module to the analyzer. Similarly, the disposal of waste fluid from the analyzer into the liquid waste container of the supply module may be coordinated with the resupply of fresh fluid from the supply module to the analyzer.

While reagents may be supplied from the supply module to the analyzer by transferring a respective reagent container, in some embodiments the reagent container remains within the supply module and only the reagent is transferred as a liquid.

In such embodiments of the method described herein, step b) further comprises establishing a fluidic connection between the supply module and the analyzer, and step d) further comprises detaching said fluid connection between the supply module and the analyzer.

Such a "fluidic connection" can be part of the robotic transferring device as described herein, or it can be a separate connection. It may be established by a variety of measures. For instance, connectors such as liquid-tight tubes or hoses may be used for transferring fresh reagents from supply module to analyzer and liquid waste from analyzer to supply module. These connectors may, for instance, be plugged to or into a port comprised by the supply module at one end and to a port comprised by the analyzer at the other end. In some embodiments, at least one of the ports comprises a valve. In some embodiments, a connector is plugged into a port comprised by a liquid waste container of the supply module at one end, and into a port comprised by a waste station of the analyzer at the other end. Accordingly, another connector may be plugged into a port comprised by a reagent container of the supply module at one end, and into a port comprised by a work cell of the analyzer at the other end. The fluidic connection is not restricted to pluggable connections, but may also comprise, for example, screw mechanisms. In some embodiments, the connection between connector and port is established with the help of a bracelet which is in some embodiments a ferrule.

"Ferrules" are mostly narrow circular rings made from metal, or less commonly, plastic. Most ferrules consist of a circular clamp used to hold together and attach fibers, wires, or posts, generally by crimping, swaging, or otherwise deforming the ferrule to permanently tighten it onto the parts that it holds.

In some embodiments, the automated analyzer comprises a waste station.

A "waste station" is the part of the automated analyzer where liquid and/or solid waste is collected. An automated analyzer may either comprise one waste station for both liquid and solid waste, which may be still collected separately within the waste station, or it may comprise a waste station for liquid waste and a separate waste station for solid waste. The waste station or stations are in some embodiments positioned next to the supply module when the latter is docked to the analyzer. In such embodiments, the transfer of the waste from the waste station to the supply module involves only a short distance.

Alternatively, the automated analyzer may function without a dedicated waste station. In such embodiments, waste incurring within the automated analyzer may be directly transferred from the place where it incurs to the respective waste container of the supply module.

In some embodiments, solid waste is transferred from the automated analyzer to the supply module by a robotic manipulator comprised by the automated analyzer. As described above, this can occur either as a transfer from a waste station to the supply module, or the robotic manipulator may collect the solid waste directly at the site where it incurs, such as in the case of a sample tube or a reaction vessel that has been processed in a work cell.

A "work cell" is a module of the automated analyzer assisting users with processing vessels containing samples such as biological samples, and thus ultimately the samples themselves. "Processing" means either detection, e.g. qualitative and/or quantitative evaluation of samples for diagnostic purposes, and/or sorting and/or preparation of samples before detection, or storing and/or disposal of samples after detection. In particular, a work cell may be related to analytical and/or to pre-analytical and/or to post-analytical sample processing steps. Work cells may be connected to each other and depend at least in part on each other, e.g. each carrying out a dedicated task of a sample processing workflow, which may be a prerequisite before proceeding to another work cell. Alternatively, work cells may work independently from each other, e.g. each carrying out a separate task, e.g. a different type of analysis on the same sample or a different sample. In general, a work cell may comprise units for loading and/or unloading and/or transporting and/or storing sample tubes or racks comprising sample tubes or multiwell plates, units for loading and/or unloading and/or transporting and/or storing reagent containers or cassettes, units for loading and/or unloading and/or transporting and/or storing and/or washing reagent vessels, e.g. cuvettes, units for loading and/or unloading and/or transporting and/or storing pipette tips or tip racks. It may comprise identification units comprising sensors, e.g. barcode or RFID readers. It may comprise wash stations for washing pipette tips or needles or reaction vessels, e.g. cuvettes, mixing paddles, or the like. The work-cell may further comprise one or more incubation units for maintaining sample/reagent mixtures at a certain temperature during reaction. The work cell may comprise a thermocycler for subjecting a sample to repeated temperature cycles and/or varying temperature conditions. Such a thermocycler may be particularly useful in the case of an analytical work cell, e.g. for conducting a polymerase chain reaction.

In an automated analyzer, a major part of the waste often incurs within the work cell or work cells. For instance, when a biological sample is prepared for chemical or biochemical such as immunochemical or nucleic acid analysis, typically isolation of a certain analyte is carried out. In some cases, nucleic acid as an analyte may be extracted from a biological sample by lysing cells or viral particles harboring it. This procedure often requires a lysis reagent and wash buffers, especially when a solid support for binding nucleic acids is involved. Such liquids are "consumed" during the procedure, meaning they are used e.g. for lysis and washing and subsequently need to be removed from the analyte to be isolated. The removed liquids are then discarded in order not to remain within the work cell, where they take up space and may constitute a potential source of cross-contamination. Hence, the liquids may be withdrawn from the sample tube or reaction vessel by a pipette using disposable pipette tips and be transferred either directly to a liquid waste container comprised by the supply module, e.g. via fluid connectors as described above, or first be transferred to a liquid waste container comprised by a waste station within the analyzer, using fluid connections as described for the connections between the supply module and parts of the analyzer. In the latter embodiment, liquid waste may be collected from different work cells and pooled in the waste station and then be centrally transferred to the supply module. This embodiment reduces the number of fluid connectors required between supply module and automated analyzer.

In some embodiments of the method described herein, step c) comprises collecting liquid waste in at least one waste container via the fluidic connection between the supply module and the analyzer.

Analogously, solid waste such as the disposable pipette tips mentioned above may be transferred directly from a work cell of the automated analyzer to a solid waste container of the supply module, or it may be first transferred within the automated analyzer from the work cell to a solid waste container comprised by the waste station of the analyzer, and then to the supply module as a bulk of solid waste, with the advantages mentioned in the context of liquid waste. Suitable transfer mechanisms for solid waste include the robotic transferring device described herein.

In embodiments where the automated analyzer comprises one or more waste containers for liquid and/or solid waste, it may also be possible that the complete respective waste containers including the waste contained therein are transferred from the automated analyzer, e.g. from the waste station of the latter, to the supply module. In these cases, the supply module may provide one or more empty unused waste containers to the automated analyzer.

Further, the supply module may either be replaced with a new supply module, or the current supply module may be undocked from the automated analyzer in order to be loaded with new, unused consumables, and in some embodiments in order remove collected waste from its waste container or containers.

Hence, in some embodiments the method described herein further comprises after step d) exchanging or re-filling at least one solid consumable and at least one reagent within the supply module and repeating steps b) to d).

Also in some embodiments, the at least one set of solid consumables within the supply module comprises one or more of the following solid consumables:
 reaction vessels
 pipette tips
 sample tubes
 cuvettes
 caps for reaction vessels
 caps for sample tubes
 binding particles for binding biological material
 filters.

Since the supply module contains reagents that may be temperature-sensitive, as well as in some embodiments other temperature-sensitive components, the supply module in some embodiments comprises a cooling system. Possible cooling systems are known to the person skilled in the art and include, without being limited to, air-conditioning, heat sinks, on-board fans, liquid cooling systems, and the like.

The supply module may in some embodiments further comprise an electronic visual display for user guidance. Such guidance may be provided, for example, when docking the supply module to the automated analyzer, or during manual exchange of the consumables in the supply module. In such embodiments, the workflow is further simplified and less training for the user is required. In addition, important information about the current content of the supply module may be shown on the display. The user may be provided with data regarding the number and type of the specific consumables currently available in the supply module. This information may be provided by a control unit and/or data management unit of the supply module.

Such an electronic visual display may likewise be comprised by the automated analyzer. A display included by the automated analyzer may inform the user about the processes performed within the analyzer. In the context of the method, system and module described herein, the display may show information regarding the status of consumables within the analyzer. The display may inform the user about a specific type of consumable to be supplied. In embodiments involving an electronic communication link between the supply module and the automated analyzer or their respective control units, the display of the automated analyzer may also show information about the supply module, such as status and availability of the consumables contained in the supply module. Further, it may be possible to manipulate the supply module docked to the automated analyzer by using the display of the automated analyzer. The automated analyzer may include means for manipulating a supply module if docked, such as dedicated buttons, or the display of the automated analyzer may itself be a touchscreen.

An electronic visual display may be based on technologies like light emission (e.g. in liquid crystal displays (LCD)), or electroluminescence (e.g. in the case of light emitting diodes (LED or OLED)), or photoluminescence (e.g. plasma display panels (PDP)), or the like. The electronic visual display may also be a touchscreen, such that the automated analyzer and/or the supply module may be directly manipulated via the display.

In another aspect, a system is described herein for supplying consumables to an automated analyzer, the system comprising the following modules:
 a supply module comprising in a predefined geometrical arrangement at least one reagent and at least one set of solid consumables, and further comprising a mount for reversibly docking the supply module to the automated analyzer
 an automated analyzer comprising a housing, the housing comprising a receiving interface for the supply module
 a work cell within the automated analyzer, the work cell being adapted to process a biological sample that may contain an analyte
 a transfer module comprising a robotic transferring device for retrieving the at least one reagent and/or the solid consumables from the supply module and transporting the at least one reagent and/or the solid consumables within the automated analyzer.

The term "biological sample" refers to a material that may potentially contain an analyte of interest. The sample can be derived from any biological source, such as a physiological fluid, including blood, saliva, ocular lens fluid, cerebrospinal fluid, sweat, urine, milk, ascites fluid, mucous, synovial fluid, peritoneal fluid, amniotic fluid, tissue, cells, or the like. The test sample can be pretreated prior to use, such as preparing plasma from blood, diluting viscous fluids, lysis or the like. Methods of treatment can involve filtration, distillation, concentration, inactivation of interfering components, and the addition of reagents. A biological sample may be used directly as obtained from the source or following a pretreatment to modify the character of the sample, e.g. after being diluted with another solution or after having been mixed with reagents e.g. to carry out one or more diagnostic assays like e.g. clinical chemistry assays, immunoassays, coagulation assays, nucleic acid testing, etc.

An "analyte" is a molecule for the detection of which analysis is conducted. Often the presence or absence of an analyte allows a medical doctor to render a diagnostic decision, i.e. to determine if the patient has a certain disease. In many cases such a diagnostic decision, however, cannot be drawn based on one analyte alone but two or more analytes have to be seen together or the result for an analyte has to be seen in the context of the clinical situation of a patient. Analytes may comprise e.g. nucleic acids, proteins, peptides, antigens, lipids, carbohydrates, glycolipids, whole cells or viral particles, or the like.

In some embodiments, the supply module further comprises at least one waste container, and the robotic transferring device is further adapted to collect waste from the automated analyzer in at least one waste container comprised by the supply module.

The parallelization of (re)supply and wasting bears the advantages disclosed in the context of the method described herein.

In some embodiments, the system described herein further comprises a fluidic connection between the supply module and the analyzer, wherein in some embodiments the fluidic connection between the supply module and the analyzer is arranged to supply reagent from the supply module to the analyzer and/or to collect fluid waste from the analyzer in the at least one waste container comprised by the supply module.

In further embodiments, the system described herein further comprises a display on the supply module and/or the automated analyzer, as disclosed in the context of the method described herein.

In some embodiments of the system described herein, the automated analyzer and/or the supply module further comprises a control unit and/or a data management unit.

In such embodiments, the system may comprise an electronic communication link between the supply module and the automated analyzer, with the advantages disclosed in the context of the method described herein.

A further aspect described herein is a supply module for supplying consumables to an automated analyzer, the supply module comprising:
at least one reagent and at least one set of solid consumables in a predefined geometrical arrangement
a mount for reversibly docking the supply module to the automated analyzer.

In some embodiments, the supply module described herein further comprises at least one waste container.

Also in some embodiments of the supply module described herein, the at least one set of solid consumables within the supply module comprises one or more of the following solid consumables: reaction vessels, pipette tips, sample tubes, cuvettes, caps for reaction vessels, caps for sample tubes, and filters.

In some embodiments, the supply module described herein further comprises a steering unit for autonomously or semi-autonomously moving the supply module, as described herein.

In further embodiments, the supply module described herein further comprises a cooling unit.

Any embodiments as exemplified in the context of the method described herein are applicable as well to the system and the supply module described herein.

It is understood that one or more of the aforementioned embodiments of the subject matter may be combined as long as the combined embodiments are not mutually exclusive.

The following non-limiting examples illustrate certain embodiments of the present subject matter.

EXAMPLES

In the following, examples are provided in order to display certain embodiments and to exemplify the subject matter described herein. It is to be understood that also other embodiments are comprised by the scope of the subject matter, as known by the person skilled in the art.

Detailed Description of the Figure

The supply module (1) depicted herein comprises elements of a drawer, such as a handle (2) for manually pulling the supply module (1) out of the analyzer or pushing it therein. The supply module further includes wheels (3) providing it with characteristics of a trolley. The wheels (3) may be passive and of purely mechanical nature, i.e. they may enable rolling the trolley by means of human force. In other embodiments, the wheels (3) may be connected to an actuator permitting movement of the supply module (1) without applying external force. The wheels (3) may be directionally fixed, or they may be rotatable around a rotational axis in order to facilitate directional changes of the moving supply module (1).

The supply module (1) further comprises mounts (4) for reversibly docking the supply module (1) to an automated analyzer by engaging the mounts (4) to a suitable structure comprised by the automated analyzer. In the depicted embodiment, the mounts (4) may be engaged to corresponding recesses within the analyzer after introducing the drawer (1) into the analyzer via a receiving interface of the latter. The recesses may include electric contacts for indicating to the control unit of the analyzer whether a supply module (1) is currently docked to the analyzer or not. The drawer (1) may be introduced into the analyzer until all consumables are within the housing of the analyzer, i.e., only the part of the supply module (1) comprising or forming the handle (2) would face the exterior of the analyzer. Thus, robotic transferring devices such as manipulators like grippers may reach the consumables of the supply module (1) within the analyzer, such that the housing of the analyzer protects the consumables from contamination. In some embodiments, the supply module (1) itself comprises a cover or a housing which may be removed prior to docking the supply module (1) to the analyzer, either automatically or manually. In other embodiments, the cover or housing of the supply module (1) may be still in place when introducing the supply module (1) into the analyzer. In these cases, the supply module (1) may include interfaces such as windows which may be opened mechanically upon introduction of the supply module (1), for example, by a hook comprised by the receiving interface of the housing, wherein the hook slides a window of the supply module (1) open during movement of the supply module (1) from the exterior towards the interior of the analyzer.

The supply module (1) in this embodiment comprises a cooling unit (5) for maintaining a suitable temperature within the supply module (1) and thereby stabilizing particularly the reagents (18, 29) contained therein. The cooling unit (5) may, for example, include Peltier elements and/or a fan. The FIGURE shows an embodiment in which liquid consumables (18, 19) and solid consumables (16) are kept in separate compartments. The liquid consumables (18, 19) are stored in the compartment comprising the cooling unit (5). The curved arrow indicates the stream of cooled air originating from the cooling unit (5) and cooling the containers with liquid consumables (18, 19). The liquid consumables (18, 19) in this embodiment include reagents (19) and a suspension of binding particles (18) in their respective containers. These containers are arranged according to a pre-determined geometry, thus allowing a robotic transferring device comprised by the analyzer and/or the supply module (1) itself to easily locate and retrieve, introduce or exchange the respective container.

Containers (17) carrying solid consumables (16) are held within a slider (6) moveable on rails (7). This sliding structure may facilitate manual loading or exchanging of the solid consumables (16) outside of the analyzer. The solid consumables (16), which may comprise racks of pipette tips, cuvettes, multiwell plates, or the like, are in this embodiment conveyed vertically in their containers (17) by an elevator (8). When solid consumables (16) have been retrieved from their containers (17), the elevator (8) may move further solid consumables (16) upwards toward the opening of the container (17), such that a robotic manipulator like a gripper may retrieve the solid consumable (16) from the container (17).

The supply module (1) further comprises a control unit (9) that manages functions and monitors the contents of the supply module (1) as described herein. The control unit (9) may also comprise a steering unit for autonomously or semi-autonomously moving the supply module (1), for example, by actuating the wheels (3) in the desired direction.

Human interaction is facilitated in this embodiment by a button (10) that may be pressed by a user. This button (10) may have different functions ranging from switching the entire electronics of the supply module (1) on or off to performing an "enter" function in an interactive computer menu. Such a menu may be shown to a user via a display (13), while the user may move a cursor on the display (13) by using separate buttons (11, 12). Further displays (14, 15) may inform the user about, for instance, the temperature within the reagent compartment, the fill status of the containers (17) with the solid consumables (16), charging status of a battery powering the supply module (1), and the like.

The supply module (1) in this embodiment further comprises solid waste containers (23) arranged on the slider (6) opposite of the solid consumable containers (17), wherein the different containers (23, 17) are separated from each other by the elevator mechanism (8). Hence, pulling out the slider (6) provides easy access for the user to both the solid waste and solid consumables (16).

Further comprised by the supply module (1) are liquid waste containers (20) each having a port (21) and a tube (22) for establishing a fluidic connection between the analyzer and the waste containers (20). The tubes (22) extend from the ports (21) to and through the mounts (4), such that the mounts (4) in this embodiment also contribute to establishing a fluidic connection with the analyzer. The respective recesses of the analyzer for receiving the mounts (4) may also be or comprise ports such that the fluidic connection is extended from the tubes (22) of the supply module (1) into and throughout the analyzer. For instance, one or more of the four depicted liquid waste containers (20) may receive liquid waste from a liquid waste station of the analyzer via the fluidic connection comprising port (21), mount (4) and tube (22) of the supply module (1) and their respective counterparts included by the analyzer. In other embodiments, some or all of the containers (20) may contain fresh reagents. In these cases, the fluidic connection may be used for transferring the reagents to a respective counterpart in the analyzer. For instance, purified water or a system buffer may be provided from a container (20) to a work cell within the analyzer.

While the foregoing embodiments have been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for supplying consumables to an automated analyzer comprising a housing, the method comprising the steps of:
   (a) providing a supply module comprising, (i) a control unit comprising sensors for liquid level detection and for determining the presence or absence of one or more types of solid consumables in the supply module; (ii) a predefined geometrical arrangement comprising at least one reagent and at least one set of solid consumables, wherein a set of solid consumables comprises one or more solid consumables of the same type; and (iii) a mount for reversibly docking the supply module to the analyzer;
   (b) reversibly docking the supply module to the analyzer using said mount and a receiving interface comprised by the housing of the analyzer;
   (c) supplying from the supply module to the analyzer at least one reagent and at least one solid consumable;
   (d) monitoring liquid levels and the presence or absence of said one or more types of solid consumables in the supply module; and
   (e) undocking the supply module from the analyzer and removing it therefrom.

2. The method of claim 1, wherein the supply module further comprises at least one waste container, and step (c) further comprises collecting waste from the analyzer in at least one waste container of the supply module.

3. The method of claim 2, wherein step (b) further comprises establishing a fluidic connection between the supply module and the analyzer, and step further comprises detaching said fluid connection between the supply module and the analyzer.

4. The method of claim 1, further comprising after step (e) exchanging or re-filling at least one solid consumable and at least one reagent within the supply module and repeating steps (b) to (e).

5. The method of claim 1, wherein the at least one set of solid consumables within the supply module comprises one or more of the following solid consumables: reaction vessels, pipette tips, sample tubes, cuvettes, caps for reaction vessels, caps for sample tubes, and/or filters.

6. A system for supplying consumables to an automated analyzer, the system comprising the following modules:
- a supply module comprising, (i) a control unit comprising sensors for liquid level detection and for determining the presence or absence of one or more types of solid consumables in the supply module; (ii) a predefined geometrical arrangement comprising at least one reagent and at least one set of solid consumables, wherein a set of solid consumables comprises one or more solid consumables of the same type; and (iii) a mount for reversibly docking the supply module to the analyzer;
- an automated analyzer comprising a housing, the housing comprising a receiving interface for the supply module;
- a work cell within the automated analyzer, the work cell being adapted to process a biological sample that may contain an analyte; and
- a transfer module comprising a robotic transferring device for retrieving the at least one reagent and/or the solid consumables from the supply module and transporting the at least one reagent and/or the solid consumables within the automated analyzer.

7. The system of claim 6, wherein the supply module further comprises at least one waste container, and the transfer module is further adapted to collect waste from the analyzer in at least one waste container of the supply module.

8. The system of claim 7, wherein a fluidic connection between the supply module and the analyzer is arranged to supply reagent from the supply module to the analyzer and/or to collect fluid waste from the analyzer in at least one liquid waste container of the supply module.

9. The system of claim 7, further comprising an electronic visual display on the supply module and/or the automated analyzer.

10. The system of claim 7, further comprising an electronic communication link between the supply module and the automated analyzer.

11. A supply module for supplying consumables to an automated analyzer, the supply module comprising:
- a control unit comprising sensors for liquid level detection and for determining the presence or absence of one or more types of solid consumables in the supply module;
- at least one reagent and at least one set of solid consumables in a predefined geometrical arrangement, wherein a set of solid consumables comprises one or more solid consumables of the same type; and
- a mount for reversibly docking the supply module to the automated analyzer.

12. The supply module of claim 11, further comprising at least one waste container.

13. The supply module of claim 11, further comprising a steering unit for autonomously or semi-autonomously moving the supply module.

14. The supply module of claim 11, further comprising wheels.

15. The supply module of claim 11, further comprising a cooling unit.

* * * * *